United States Patent

Brassington

Patent Number: 5,296,290
Date of Patent: Mar. 22, 1994

[54] ABSORBENT LAMINATES

[75] Inventor: Nigel J. Brassington, Keighley, United Kingdom

[73] Assignee: Johnson & Johnson, New Brunswick, N.J.

[21] Appl. No.: 23,740

[22] Filed: Feb. 26, 1993

Related U.S. Application Data

[63] Continuation of Ser. No. 769,509, Oct. 1, 1991, abandoned, which is a continuation of Ser. No. 545,671, Jun. 8, 1990, abandoned, which is a continuation of Ser. No. 784,290, Sep. 24, 1985, abandoned.

[30] Foreign Application Priority Data

Jan. 26, 1984 [GB] United Kingdom ............. 8402095

[51] Int. Cl.$^5$ ................................................ B32B 5/06
[52] U.S. Cl. .................................... 428/300; 428/284; 428/287; 604/383
[58] Field of Search ............. 428/280, 282, 284, 287, 428/300; 604/383

[56] References Cited

U.S. PATENT DOCUMENTS

| | | | |
|---|---|---|---|
| 30,972 | 6/1982 | Kyle et al. | 428/300 |
| 3,545,442 | 12/1970 | Wicker et al. | 428/300 |
| 3,811,445 | 5/1974 | Dostal | 128/285 |
| 4,424,247 | 1/1984 | Erickson | 428/283 X |
| 4,424,248 | 1/1984 | Tesch et al. | 428/283 X |
| 4,469,740 | 9/1984 | Bailly | 428/300 X |
| 4,495,235 | 1/1985 | Tesch | 428/300 X |
| 4,503,116 | 3/1985 | Lapidus | 428/300 X |
| 4,530,869 | 7/1985 | Tesch | 428/300 X |
| 4,537,822 | 8/1985 | Nanri et al. | 428/300 |
| 4,539,982 | 9/1985 | Bailly | 428/300 X |
| 4,759,976 | 7/1988 | Dutt | 428/259 |

FOREIGN PATENT DOCUMENTS

| | | |
|---|---|---|
| 199727 | 5/1983 | New Zealand . |
| 183103 | 1/1989 | New Zealand . |
| 2081320 | 2/1982 | United Kingdom . |

*Primary Examiner*—James J. Bell

[57] ABSTRACT

Absorbent laminates, which may be used as or in diapers, incontinence pads, sanitary napkins, tampons or wound dressings, comprise a hydrophilic layer adjacent a water-permeable fibrous web. Fluid-transporting wicks extend from within the fibrous web into the hydrophilic layer, and are preferably formed by needling. The hydrophilic layer is preferably a peat moss composite board, and the fibrous web is preferably a nonwoven polyester fleece.

6 Claims, 1 Drawing Sheet

ABSORBENT LAMINATES

This invention relates to absorbent laminates, especially for use as or in products for absorbing body fluids, such as diapers, incontinence pads, sanitary napkins, tampons and wound dressings.

Characteristics which are desirable in most absorbent products are high absorbency (i.e. the capacity to absorb large quantities of fluid per unit weight of absorbent), and a high rate of fluid uptake. It is generally also desirable for the absorbent material to have a high degree of fluid retention, so that absorbed fluid is not readily released when the product is subjected to externally applied pressure.

The present invention provides absorbent laminates which not only possess the above described characteristics, but also the capacity to transfer fluid rapidly away from a layer which is initially wetted, into an adjacent layer, leaving the first layer substantially dry to the touch. This latter characteristic is especially desirable in incontinence aids, because it gives greatly increased user comfort.

According to the present invention there is provided an absorbent laminate comprising a fluid-permeable first layer formed of a hydrophobic fibrous material, an absorbent hydrophilic layer adjacent thereto, and a plurality of fibres extending from within the first layer into the hydrophilic layer.

As will be appreciated by those skilled in the art, the term "hydrophilic" is used to describe materials which are wetted by water, (i.e. materials which have contact angles with water less than 90°), while the term "hydrophobic" is used to describe materials which are not wetted by water (i.e. materials which have contact angles equal to or greater than 90°).

The fibres which extend between the two layers serve as wicks along which aqueous fluids may be carried from the first layer into the hydrophilic layer. The use of fluid-transferring wicks in absorbent products is not in itself new. For example, British Patent Specification No. 983576 describes an absorbent body comprising a cellular sponge having numerous closely spaced hydrophilic fibres extending from at least one surface into the main body of the sponge, the hydrophilic fibres being uncoated by the material of the sponge and forming channels acting to wick fluids from the surface of the cellular sponge material into the main body thereof.

A principal object of the invention described in the above-mentioned specification is to allow hydrophobic sponges to be used as padding materials in surgical dressings, without their acting as barriers to the uptake of wound exudates. Thus, in the preferred embodiment of the invention described in Specification No. 983576, the hydrophilic fibres pass completely through the sheet of sponge material, so that the fibres act to draw aqueous fluids from the wound-contacting side of the sponge sheet through to the opposite surface where they are absorbed by an appropriate absorbent layer.

In the laminates of the present invention, the wicks serve not to provide fluid paths through an otherwise water-repellent layer, but to enhance fluid transfer between two water-absorbent layers.

Examples of fibrous materials which may be used for the first layer and for the wicks extending into the adjacent layer are polyolefins such as polyethylene, polypropylene and polybutylene homopolymers and co-polymers, vinyl polymers such as polyvinylchloride, polyamides such as nylon, and polyesters. Of course, it is also possible to use fibres of materials which are in themselves hydrophilic, if such fibres are first surface-treated in order to render them hydrophobic.

Preferably, the fibrous hydrophobic layer is in the form of a nonwoven fibrous fleece, which may, if desired, be pre-needled in order to increase its coherence.

Examples of materials which may be used to form the absorbent hydrophilic layer include swellable acrylate polymers, swellable cellulosic polymers (these two groups sometimes being referred to as "superabsorbents" or "super retention agents"), peat moss board, sphagnum, absorbent inorganic materials, fluff pulp, absorbent papers and hydrophilic foamed polymers such as hydrophilic polyurethane foams. A material which is particularly preferred is a peat moss composite board such as that described in British Patent Specification No. 2081320.

The wicks which extend from the first layer into the adjacent layer may be formed in a number of ways. Such wicks may be formed, for example, by stitch bonding the two layers together. Preferably, however, the hydrophobic fibres of the first layer are themselves used to form the wicks by needling the hydrophobic fibrous layer to the adjacent hydrophilic layer. Needling is a process known per se as a means of laminating fibrous webs, and generally involves passing barbed needles into and out of a fibrous web in a reciprocating motion. Fibres from within the web are caught on the barbs of the needles, and are either pushed forward with the forward movement of the needle, or drawn back with the reverse movement of the needle, or both, depending on the type of needle used. The density of needling is chosen according to the strength and fluid transport properties which are desired in the resulting laminate. Increasing the density of needling increases the number of wicks extending between the two layers, and thereby increases the rate of fluid transfer from the facing layer to the adjacent layer. Increasing the density of needling also increases resistance to delamination.

On the other hand, increased density of needling also tends to produce greater compaction of the absorbent layers, resulting in a decrease of the overall absorbent capacity, as well as an increase in the rigidity of the resulting product. This latter factor is of particular importance in cases where the increased rigidity may lead to user discomfort, such as may be the case, for example, if the laminates of the invention are used as incontinence pads.

Usually, needling will be conducted at a density of at least 1 needle/cm$^2$, and more usually at a density of from 2 to 20 needles/cm$^2$. A needle density of from 5 to 15 needles/cm$^2$ is particularly preferred.

For some purposes, it will be appropriate to employ a needling density which is not constant over the whole area of the laminate. For example, a higher density of needling may be employed at the edges of an absorbent pad according to the invention, since it is here that greatest resistance to delamination is most likely to be required. Thus, it may be appropriate to needle a pad for use as a wound dressing at a density of 8 needles/cm$^2$ over its central area, and at a density of 12 or more needles/cm$^2$ at its edges.

The laminate may be needled on one or both faces of the hydrophilic layer, -and the needles may penetrate the hydrophilic layer completely or just partially.

When a relatively friable hydrophilic absorbent material (such as peat moss board) is used as the absorbent layer in laminates-of the invention, we have found that standard needling processes can lead to laminates with a machine direction strength which may be inadequate for certain purposes, such as when the laminates are used as incontinence pads. When such pads are worn by ambulant patients, considerable shear forces can be set up in the machine direction by the action of walking, resulting in the pad being stretched. When an unstrengthened needled laminate is used, this stretching can cause the absorbent layer to fracture. Such fracture is highly deleterious to the absorbent properties of the laminate, such as its strike-through time and the speed of surface drying. This type of fracture can be made less likely by strengthening the laminate. Strengthening can be provided by including within the laminate an extra layer comprising an inextensible or relatively inextensible web or net However, a greatly preferred method is to include strengthening threads along the length (i.e. along the machine direction) of the laminate. These threads should be "furry", for example threads of the type called "Bouclé". The furry exterior of these threads can then become entangled within the needled wicks passing perpendicularly through the laminate. The result of providing such threads at 1 cm intervals is to more than double the force required to fracture peat moss board, thus rendering the laminate more suitable for use as incontinence pads.

It will be understood that needling, although preferred, is not the only means by which fibres from within the fibrous layer can be caused to form wicks in accordance with the invention. For example, wicks may be formed by means of very fine, high pressure water jets directed at one or both free faces of two superimposed fibrous webs, as more fully described in U.S. Pat. Nos. 2,862,251 and 3,033,721.

The absorbent capacity required of the laminate will, of course, depend on the end use to which it is to be put. Generally, however, it is preferred that both the hydrophilic layer and the hydrophobic layer are capable of absorbing more than 5 grams of water per gram of absorbent. More preferably, the absorbent capacities of the core layer and the facing layer are both greater than 8 grams of water/gram of absorbent, for example 10 or more grams of water/gram of absorbent.

The hydrophobic layer should preferably be extremely permeable to fluids, so as to allow passage of fluid under gravity at a rate of at least 10 ml of fluid/second/cm$^2$ without surface puddling, and more preferably at greater than 20 ml/sec/cm$^2$, e.g. 30 ml/sec/cm$^2$. This is especially desirable when the laminate is used as an incontinence pad, so that urine can be absorbed even at full flow.

It will be appreciated that the absorbent products according to the present invention will usually incorporate further layers in addition to the two layers described above. Usually, the hydrophilic layer will be sandwiched between at least two further layers. In some applications, such as diapers, it may be desirable to cover one of the faces of the hydrophilic layer with a fluid-repellent layer such as plastics sheeting. More usually, both faces of the hydrophilic layer will be covered with an absorbent layer, which may be of the same or different materials as each other, and of the same or different thickness and/or weight. For example, the hydrophilic layer may have one face covered with a polyester fibre web, and the other face covered with a viscose fibre web.

A particularly advantageous product according to the invention comprises a central core of peat moss board, such as BISHOP (Trade Mark) board, sandwiched between webs of polyester fibre. Peat moss board is known from British Patent Specification No. 2081320 to be highly absorbent, but it does have some disadvantages, such as lack of strength and friability. Also, it has a fairly high bulk rigidity as a result of calendering in its manufacture. A needled laminate of peat moss board with non-woven polyester fibre webs is found to have high tensile strengths, even when wet, in both the machine and cross directions, especially when reinforced by Bouclé threads as above described. Moreover, the laminate is soft and conformable. The polyester fibre webs are capable of absorbing fluids at extremely high rates, and such absorbed fluid is quickly transferred to the peat moss board by means of the wicks formed during the needling operation. Thus, the polyester fibre webs are found to dry out within a very short time (e.g. of the order of 1 minute) of being wetted. The product is also found to have a highly delayed strike-through rate. It is believed that this is part due to the swelling of the peat moss board on wetting, such swelling serving to restrict the pores formed through the board by the needling operation, thereby preventing wicking through to the opposite face of the product from the face which is wetted.

Peat moss board has the additional advantage of being somewhat deodorant, which is of great value in certain absorbent products, particularly incontinence pads and sanitary napkins.

Although peat moss board is naturally friable and produces a substantial quantity of fines, the open fluffy nature of the outer polyester webs tends to trap any fines generated, without the need for any coverstock. This is especially so if the peat moss board is entirely enclosed by the polyester fibre web, as is preferred for incontinence pads. The benefit of fully enclosing the peat moss board is largely aesthetic, but a secondary advantage is that damp or wet absorbent material is prevented from contacting the wearer's skin or clothing. Such a fully enclosed structure may be formed by intermittently feeding sections of peat moss board onto a continuous web of polyester fibre, covering the peat moss board with a second continuous polyester fibre web, needling and then severing the resulting laminate between the sections of peat moss board.

The absence of any coverstock can be advantageous in certain applications, such as when the absorbent product is used as an incontinence pad. Coverstocks reduce the rate of fluid uptake, add considerably to the cost and can lead to abrasion. Where a high rate of fluid uptake is less critical, such as in sanitary napkins, a coverstock can be used to enhance the appearance of the product.

When a laminate comprising peat moss board and a loose polyester fibre web are used in a wound dressing, it is preferable to provide a low adherence wound contacting surface, such as a spun bound polyester fabric.

In general, peat moss board will be used in weights of from 100 g/m$^2$ to 1 kg/m$^2$, and preferably from 300 to 500 g/m$^2$. As mentioned above, however, the actual weight used, and that of the hydrophobic fibrous layer, will depend on the end use to which the laminate is to be put. For sanitary protection aids or wound dressings, for example, it is preferred to use a light weight peat moss board (160 g/m²) surrounded by the lightest weight polyester fleece that is practical (e.g. 80 g/m²). The density of needling should also be fairly light (e.g. 8 needles/cm²) to give a noticeably "furry" surface, the preferred polyester fleeces also being pre-needled at this density. This construction is preferred for sanitary protection aids and wound dressings for the following reasons: The fleece has a surface which can contact well with any coverstock placed over it; the very light fleece is adequate to obscure the peat moss board and to trap any fines; the laminate is not too bulky, and is highly flexible and conformable; the thin polyester fleece has very rapid surface drying properties (the surface being dry to the touch within a few seconds of being wetted).

For incontinence pads it is preferred to use a heavier weight peat moss board surrounded by a thicker polyester fleece which has been more heavily pre-needled. The preferred construction is a 360 g/m² microcreped peat moss board with 180 g/m² polyester fleeces (pre-needled at 12 needles/cm²) laminated on both sides using 12 needles/cm². This construction has the following advantages: The total absorbency is appropriate to the needs of patients with stress or other forms of light voiding incontinence; the surface is coherent and does not require a coverstock; the fleeces are thick enough to hold considerable quantities of fluid in the short time before it is fully absorbed by the peat moss board; the thicker fleeces also give a high degree of cushioning.

For incontinence pads for patients with detrusor instability or other forms of rapid voiding incontinence, it is preferred to use even heavier peat moss board (e.g. 500 g/m²) or multiple layers of lighter board (e.g. two or three layers of 330 g/m² board).

Absorbent laminates according to the present invention are now described, by way of example, with reference to the accompanying drawings, in which.

Figure 1:
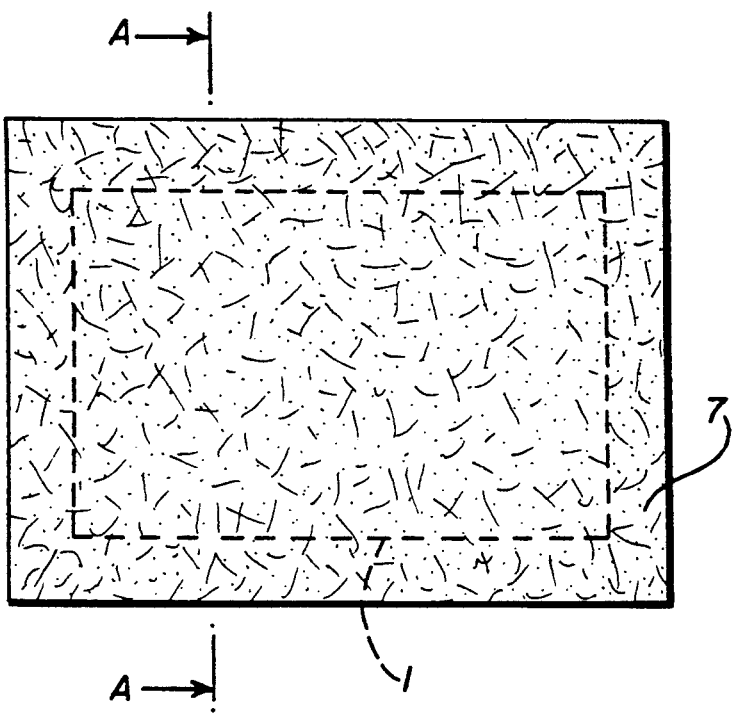
FIG. 1 is a plan view of an absorbent laminate according to the invention.
Figure 2:
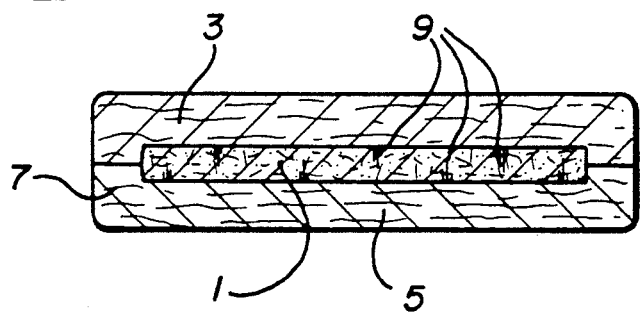
FIG. 2 is a schematic section on line A—A of FIG. 1.

Referring to FIGS. 1 and 2 of the drawings, an absorbent laminate comprises a core layer 1, sandwiched between two facing layers 3, 5. The core layer 1 is a rectangular section of peat moss board of weight 330 g/m², manufactured according to British Patent Specification No. 2081320. This material is typically able to absorb 10 times its own weight of water. The facing layers 3, 5 are both non-woven pre-needled polyester fibre fleeces of weight 250 g/m², (Cosmopolitan Textiles Ltd., Winsford, Cheshire, England). Fleeces of widely different weights could, of course, be used, but weights within the range 100 to 500 g/m² are preferred. Each of the facing layers overlaps all four sides of the core layer, so that the latter is entirely enclosed and is surrounded by an edge region 7.

The three layers 1, 3, 5 are joined by needling at a density of 8 needles/cm². This needling operation forms wicks 9 of polyester fibre which extend from the facing layers 3, 5 into the core layer 1. The edge region 7 is needled at a density of 12 needles/cm², to form a strong bond between the peripheral areas of the facing layers.

Figure 3:
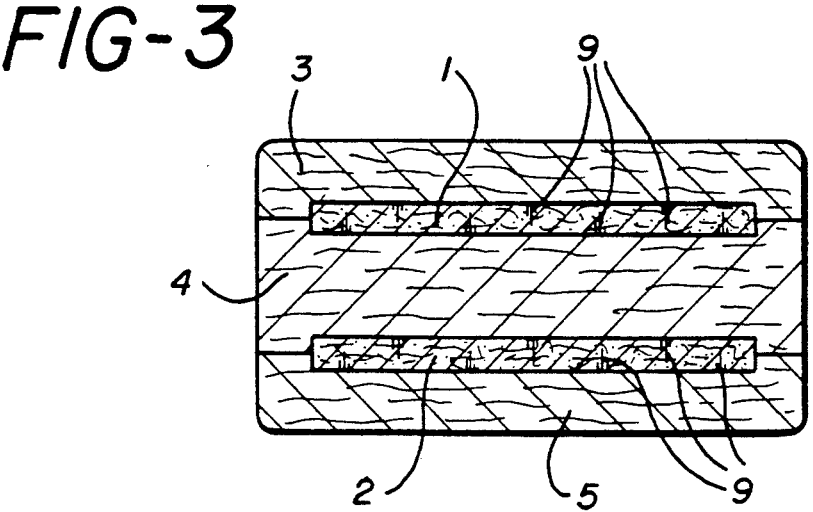
FIG. 3 is a schematic section through an alternative absorbent laminate.

FIG. 3 illustrates a laminate which is analogous to that of Fibres 1 and 2, but differs in that two core layers of peat moss board 1, 2 are provided, with three facing layers 3, 4, 5 of polyester fibre web.

The present invention is further illustrated by the following examples.

EXAMPLE 1

A three layer laminate is formed from the following materials:

| Layer 1. | Pre-needled (8 needles/cm²) polyester fleece, 130 g/m². |
|---|---|
| Layer 2. | Peat moss board, made as described in British Patent Specification No. 2081320, 330 g/m². |
| Layer 3. | As layer 1. |

The layers were joined by needling at 8 needles/cm², and the absorbent characteristics of the resulting laminate were tested by applying 20 mls of physiological saline solution to one surface of the laminate in one second. (This fluid is a synthetic aqueous composition containing 0.9% sodium chloride in distilled water). Within 2 minutes, the wetted surface of the laminate was found to be dry to the touch.

By way of comparison, a similar laminate which had not been needled was subjected to the same test. The wetted surface was found to remain damp to the touch for at least 10 minutes, and in some cases up to 2 hours after being wetted.

EXAMPLE 2

A laminate was prepared as described in Example 1, except that polyester fleeces of 100 g/cm² were used in place of the heavier fleeces described therein. The strike-through time and absorbency of the laminate were tested as follows:

The laminate was sandwiched between two transparent PERSPEX (Trade Mark) plates, the lower of which was provided with a hole for the application of test fluid to the laminate under a small (e.g. 0.5 cm) hydrostatic head. The strike-through time of the laminate was the time taken for such applied fluid to contact the upper PERSPEX plate, as detected by the specular appearance of the latter when first wetted.

It was found that the strike-through time of the laminate was 180 seconds, at which time 18.0 g of Meds fluid had been absorbed.

When a three-layer laminate was formed using 100 g/m² viscose fleeces in place of polyester fleeces, the strike-through time was reduced to 15 seconds, at which time only 1.8 g of Meds fluid had been absorbed. Moreover, the surface of this laminate remained damp to the touch, even several hours after having been wetted.

EXAMPLE 3

This example shows the effects of different needle densities on absorbency and other properties of the laminate.

Two laminates were made from peat moss board (320 g/m²) having polyester fleeces (100 g/m²) needled to each surface. The first laminate was needled at 8 needles/cm² (light tack), and the second at 12 needles/cm² (medium tack), and the two products tested for absorptive capacity (Meds fluid), wicking ability and tensile strength. The results were as follows:

|                          | LIGHT TACK   | MEDIUM TACK  |
|--------------------------|--------------|--------------|
| Absorptive Capacity      | 14.3 g/g     | 13.1 g/g     |
| Machine Direction Wicking| 6.2 g        | 6.4 g        |
|                          | 9 mm         | 13 mm        |
| Cross Direction Wicking  | 6.8 g        | 5.9 g        |
|                          | 8 mm         | 12 mm        |
| Tensile strength         |              |              |
| (Machine Direction)      | 1.1 Kg/5 cm  | 1.0 Kg/5 cm  |
| (Cross Direction)        | 1.7 Kg/5 cm  | 1.4 Kg/5 cm  |

It will be seen that increased needle density increases the wicking distance of the laminate, but decreases the absorptive capacity and tensile strength.

The polyester fibre used in the above Examples was a surface-treated polyethylene terephthalate (ICI type 578). The surface-treatment was with a mixture of oleyl cetyl alcohol and castor oil ethylene oxide condensates with sodium benzoate, potassium hexyl phosphate and propanol.

It will be understood that the present invention is described above merely by way of example, and numerous variations may be made without departing from the scope of the invention.

I claim:

1. An absorbent laminate for absorbing aqueous body fluids comprising a first layer formed of hydrophobic fibers and pervious to said aqueous body fluids; a water absorbent hydrophilic layer adjacent thereto; and a plurality of said hydrophobic fibers extending from within said first layer into said hydrophilic layer wherein the plurality of fibers extending from within the first layer into the hydrophilic layer are formed from the material of the first layer by needling at a density of from 5 to 20 needles/cm$^2$.

2. An absorbent layer according to claim 1 wherein the hydrophilic layer is formed from peat moss board, a swellable acrylate or cellulosic polymer, sphagnum, an absorbent inorganic material, fluff pulp, absorbent paper or a hydrophilic foamed polymer.

3. An absorbent layer according to claim 1 wherein the hydrophobic fibers are polyolefin, vinyl polymer, polyamide or polyester fibers.

4. An absorbent elminate according to claim 1 wherein said hydrophilic layer has laminated thereto, on the surface opposite from said first layer, a further absorbent layer.

5. An absorbent laminate according to claim 1 comprising a layer of peat moss board having laminated to each major surface thereof a fluid-permeable nonwoven polyester fiber fleece.

6. A diaper, incontinence pad, sanitary napkin, tampon or wound dressing comprising or consisting of a laminate according to claim 1.

* * * * *